(12) United States Patent
Dekel et al.

(10) Patent No.: US 7,996,495 B2
(45) Date of Patent: Aug. 9, 2011

(54) ADAPTIVE SELECTION OF IMAGE STREAMING MODE

(75) Inventors: Shai Dekel, Ramat-Hasharon (IL); Alexander Sherman, Modihin (IL); Roni Zaharia, Tel-Aviv (IL)

(73) Assignee: General Electric Company, Schenectady, NY (US)

(*) Notice: Subject to any disclaimer, the term of this patent is extended or adjusted under 35 U.S.C. 154(b) by 1097 days.

(21) Appl. No.: 11/400,496

(22) Filed: Apr. 6, 2006

(65) Prior Publication Data

US 2007/0237402 A1 Oct. 11, 2007

(51) Int. Cl.
G06F 15/16 (2006.01)
G06F 15/173 (2006.01)
G06K 9/36 (2006.01)

(52) U.S. Cl. ......... 709/219; 709/225; 709/232; 382/232
(58) Field of Classification Search ................... 709/219; 382/128, 232, 276
See application file for complete search history.

(56) References Cited

U.S. PATENT DOCUMENTS

| | | | |
|---|---|---|---|
| 5,235,419 A | 8/1993 | Krause |
| 5,276,898 A | 1/1994 | Kiel et al. |
| 5,392,223 A | 2/1995 | Caci |
| 5,619,685 A | 4/1997 | Schiavone |
| 5,675,789 A | 10/1997 | Ishii et al. |
| 5,689,800 A | 11/1997 | Downs |
| 5,761,438 A | 6/1998 | Sasaki |
| 5,764,235 A | 6/1998 | Hunt et al. |
| 5,931,904 A | 8/1999 | Banga et al. |
| 5,983,263 A | 11/1999 | Rothrock et al. |
| 6,112,250 A | 8/2000 | Appelman |
| 6,138,147 A | 10/2000 | Weaver et al. |
| 6,243,761 B1 | 6/2001 | Mogul et al. |
| 6,314,452 B1 | 11/2001 | Dekel et al. |
| 6,385,656 B1 | 5/2002 | Appelman |
| 6,453,355 B1 | 9/2002 | Jones et al. |
| 6,512,778 B1 | 1/2003 | Jones et al. |
| 6,633,609 B1 | 10/2003 | Ing et al. |
| 6,704,024 B2 | 3/2004 | Robotham et al. |
| 6,708,220 B1 | 3/2004 | Olin |
| 6,799,251 B1 | 9/2004 | Jacobs et al. |

(Continued)

FOREIGN PATENT DOCUMENTS

WO 2004/102949 A1 11/2004

(Continued)

OTHER PUBLICATIONS

Chandra, S. et al., Application-Level Differentiated Multimedia Web Services Using Quality Aware Transcoding, 18 IEEE Journal on Communications, Dec. 12, 2000, pp. 2544-2565, ISSN 0733-8716.

(Continued)

*Primary Examiner* — Wing Chan
*Assistant Examiner* — David Yi
(74) *Attorney, Agent, or Firm* — Andrus, Sceales, Starke & Sawall, LLP

(57) ABSTRACT

A Picture Archiving and Communications System (PACS) transmits medical image information from a server to a viewing workstation. The mode of transmission that the system uses depends on a performance metric of the network. If the network is fast and stable, the entire DICOM image file is transmitted. If the network is not fast and stable, one of several other modes is used to transmit the image information.

17 Claims, 2 Drawing Sheets

U.S. PATENT DOCUMENTS

| | | |
|---|---|---|
| 6,829,648 B1 | 12/2004 | Jones et al. |
| 6,848,004 B1 | 1/2005 | Chang et al. |
| 6,880,003 B2 | 4/2005 | Greenwood |
| 6,909,436 B1 | 6/2005 | Pianykh |
| 2001/0029523 A1 | 10/2001 | McTernan et al. |
| 2001/0038638 A1 | 11/2001 | Slowe et al. |
| 2001/0044851 A1 | 11/2001 | Rothman et al. |
| 2001/0047422 A1 | 11/2001 | McTernan et al. |
| 2002/0078241 A1 | 6/2002 | Vidal et al. |
| 2004/0261135 A1 | 12/2004 | Cahnbley et al. |
| 2005/0132045 A1* | 6/2005 | Hornback et al. ............ 709/225 |
| 2005/0132068 A1* | 6/2005 | Rajamony ................... 709/228 |

FOREIGN PATENT DOCUMENTS

| | | |
|---|---|---|
| WO | 2007/038187 A2 | 4/2007 |

OTHER PUBLICATIONS

Gaddah et al., Image transcoding proxy for mobile Internet access, Proceedings of the Vehicular Technology Conference 2002, Sep. 2002, pp. 807-811, ISSN 1090-3038. Abstract only.

Lee et al., SIQuA: server-aware image quality adaptation for optimizing server latency and capacity in wireless image data services [mobile radio[, Vehicular Technology Conference, 2004, 4 VTC2004-Fall (IEEE), pp. 2611-2615, ISSN 1090-3038. Abstract only.

Kim et al., A new resource allocation scheme based on a PSNR criterion for wireless video transmission to stationary receivers over Gaussian channels, IEEE Transactions on Wireless Communications 1:3, Jul. 2002, pp. 383-401, ISSN 1536-1276. Abstract only.

Raman et al., ITP: an image transport protocol for the Internet, IEEE/ACM Transactions on Networking 10:3, Jun. 2002, pp. 297-307, ISSN 1063-6692; U.S. Patents No. 5,931,904 and 5,276,898. Abstract only.

European Search Report dated Jul. 23, 2007.

Taubman et al., "JPEG2000 Image Compression Fundamentals, Standards and Practice", 2004, Kluwer Academic Publishers, ISBN: 0-7923-7519-X, pp. 637-641.

Sanchez et al., "Prioritized Region of Interest Coding in JPEG2000", IEEE Transactions on Circuits and Systems for Video Technology, vol. 14, No. 9, Sep. 2004, pp. 1149-1155.

Banitsas et al., "Adjusting DICOM Specifications When Using Wireless LANs: The MedLAN example", Proceedings of the 25th Annual Int'l. Conf. of the IEEE EMBS, vol. 4 of 4, Conf. 25, Sep. 17, 2003, pp. 3661-3664.

Makris et al., "Teleworks: A CSCW Application for Remote Medical Diagnosis Support and Teleconsultation" IEEE Transactions on Information Technology in Biomedicine, Jun. 1998, vol. 2, No. 2, pp. 63-73.

Naftali et al., "Wireless Telemedicine Systems: An Overview", Wireless Corner, IEEE Antennas and Propagation Magazine, Apr. 2002, vol. 44, No. 2, pp. 143-153.

"Prioritized Region of Interest Coding in JPEG2000", Victor Sanchez et al., IEEE Transactions on Circuits and System for Video Technology, vol. 14, No. 9, pp. 1149-1155, Sep. 30, 2004.

Chinese Office Action dated Nov. 11, 2010.

* cited by examiner

ADAPTIVE SELECTION OF IMAGE STREAMING MODE

BACKGROUND OF THE INVENTION

1. Field of the Invention

This invention relates generally to the storage, archiving, networking, and retrieval of medical images and video, and more particularly to improvements in a Picture Archiving and Communications System (PACS) operating in networks having different possible bandwidths.

2. Description of the Related Arts

A PACS is a system for the storage, retrieval, and display of medical images. A PACS typically consists of one or more networked computers along with a substantial amount of semi-permanent digital storage in the form of, for instance, a RAID (redundant array of inexpensive hard disks), tape storage, or optical disks. A PACS also typically includes software for storing, retrieving, and displaying images, along with hardware that may be necessary for physical management of digital media (e.g., a robotic tape loader), display, and input.

A PACS is typically connected to an imaging device such as a CT (computerized tomography) scanner, an MRI (magnetic resonance imaging) scanner, or an X-ray machine capable of providing images in digital format, often including images compliant with the DICOM (Digital Imaging and Communications in Medicine) format. A doctor or other health care provider uses the imaging device to create a digital picture of a patient for diagnosis or treatment purposes. The image is delivered via a network to the PACS, where it is stored along with information identifying the particular patient. The image is viewed on the PACS immediately or it is retrieved for display later. The image is optionally processed prior to storage, or it is stored in a raw digital format and subjected to optional processing later.

Prior to the development of PACS technology, hospitals typically stored medical images on film that had to be catalogued and retrieved by hand. Early computerized medical imaging devices were flawed because the machines were typically standalone devices with no or limited archival capabilities and proprietary file formats. PACS, along with the standard DICOM and other file formats, provided a convenient, standardized way to store medical images with fast, electronic retrieval, more convenient backup, and potential for remote electronic distribution.

Despite their advantages, traditional PACSs have numerous shortcomings. First, a traditional PACS may operate in connection with various different networks, each of which has a different bandwidth, or even with a single network having an effective bandwidth that varies with overhead requirements, competing data traffic from other systems using the same network, and the like.

Known PACSs are configured to stream images using any of a number of data transfer protocols. Some protocols are particularly well adapted for high bandwidth networks, while others typically are optimized to work with lower bandwidth networks. Commonly, optimizing a protocol for a particular network bandwidth calls for certain design tradeoffs. For example, high bandwidth channels permit the transfer of image data with very little preprocessing or post processing, thus imposing very little overhead on the devices used to store, retrieve, package, transmit, receive, and decode the data. Other communication channels, for example wireless channels, may have a very wide bandwidth but suffer from periodic network failures, for example when a device's wireless communications path is blocked by other equipment or where the device gets out of range of the node it is communicating with. Still other channels, such as networks relying on conventional modem communications over telephone networks, particularly older POTS ("Plain old telephone service") networks, have far less bandwidth. To achieve satisfactory image streaming using such low-bandwidth networks, significant data compression/decompression must be used, typically calling for significant processing resources.

In many instances, it may be acceptable to choose a likely network bandwidth for a PACS implementation, and select communication protocols that are optimized to work with such expected network. However, experience has shown that quite often such systems will end up operating under various network bandwidths, and it would be advantageous to have a PACS that could operate effectively in connection with a variety of network bandwidths.

Considering the situation in greater detail, medical images shared across one or more healthcare organizations are commonly stored in the DICOM format, which supports a variety of data representations, including raw pixel data, baseline lossless compression (lossless JPEG), and the progressive compression standard known as JPEG 2000. Healthcare organization network infrastructures often suffer from bottlenecks, insufficiencies, instabilities and other problems that make image streaming using a preferred format impossible, for example because the images cannot be fetched and rendered at a user's viewing workstation fast enough to appear in real time.

Simple known solutions, such as increasing network bandwidth, are not always feasible, due to a variety of factors ranging from cost to hospital wiring policies.

Another possibility is conventional compression of the image data to be streamed. In many medical applications, however, some types of compression, particularly lossy compression, are either disfavored or outright forbidden. The concern is that medical diagnostic work is too important and subtle a task to be burdened with additional uncertainties that may arise by intentionally degrading an image from its original number of pixels, bit depth, and other characteristics. Lossless compression techniques, even when they are allowed, typically only reduce image file sizes by less than an order of magnitude, which in many cases is not sufficient to provide real time streaming over low bandwidth channels. Medical images are particularly ill-suited to lossless compression because many medical imaging modalities such as CT or ultrasound inherently produce images having significant pure noise components that do not lend themselves to significant compression using known lossless methods.

Even where compression is workable, difficulties remain to be addressed. For example, the wavelet-based JPEG2000 image compression standard provides progressive compression capabilities that allow the transmission of images in separate "layers" of quality. An initially transmitted image improves with quality as more data arrive. In "lossless" mode, JPEG2000 processing allows transmission of the data until the received image is of the same quality as the original image. In some circumstances, use of this format provides some manner of inherent adaptability to varying bandwidths, as once bandwidth drops below the size needed for real time lossless transmission, transmission simply continues at somewhat lower quality, with images being discarded before they reach original-image quality.

A further known improvement using JPEG2000 is to transmit high quality images for only a particular region of interest (ROI) when full-bandwidth original-quality transmission is not possible.

These solutions may be available where original images are available in a DICOM format compliant with JPEG2000, but many imaging modalities do not make images available in such format. Even where such images are available, lossless JPEG2000 coding is computationally demanding, typically 5-6 times slower than comparable lossless coding under the previous JPEG standard. Correspondingly, decoding and rendering of such JPEG2000 images is likewise more computationally intensive, and may result in unacceptable performance on conventional viewing workstations.

U.S. Pat. No. 6,314,452 discloses one partial solution to the difficulties in using JPEG2000 using wavelet streaming. However, this and others of the known techniques still impose unnecessary overhead, for instance by still coding/decoding images when wide network bandwidths are available and image transfer could be accomplished without this additional processing.

Some on-demand video applications also address similar issues through scalable video streaming and quality of service. Using the advanced capabilities of the MPEG video compression standard, one can control the rate/distortion tradeoff on a per-device (i.e., viewing device) basis. Accordingly, one can dynamically allocate a bitstream among various viewing nodes and stream higher resolution video to higher resolution viewing devices and higher visual quality to certain users. However, these solutions typically assume that video is streamed from a single pre-processed MPEG file composed of resolution and quality layers—an assumption that is often not true in many medical applications.

In medical tele-radiology applications, the traditional solution has been to schedule transfers of large lossless DICOM images in advance, during off-peak hours, so that a radiologist or other provider can receive, store, and later review the images. Various techniques are used to try to predict when off-peak slots will be available and match that with the healthcare needs associated with the images to be transmitted.

U.S. Pat. No. 6,848,004 discloses a system for adaptive delivery of rich-media content in web pages. This document discloses a client-server system in which the client calculates the bandwidth and the server adaptively transmits web content, with richer content being transmitted when higher bandwidth is available. This technique relies on the availability of dynamically loading applet technologies, such as JAVA applets, that may not be available in all situations.

Likewise, U.S. Pat. No. 6,243,761 discloses a method for dynamically adjusting multimedia content of a web page by a server according to effective bandwidth and/or latency characteristics. In this instance, the content sent to the client computer is adjusted, such as by reducing the size, resolution, or number of images of the graphic image. While such modification of content might be acceptable in many web-browser applications, it may not be appropriate for many medical applications.

Another approach is described in Chandra, S. et al., Application-level differentiated multimedia Web services using quality aware transcoding, 18 IEEE Journal on Communications 12, December 2000, pp. 2544-2565, ISSN 0733-8716 ("Chandra"). Chandra discloses use of application-specific characteristics of Web services to manage resources. Again, the environments of typical PACSs may not make such services available. Still other disclosures addressing some of these issues are Gaddah et al., Image transcoding proxy for mobile Internet access, Proceedings of the Vehicular Technology Conference 2002, September 2002, pp. 807-811, ISSN 1090-3038; Lee et al., SIQuA: server-aware image quality adaptation for optimizing server latency and capacity in wireless image data services [mobile radio], Vehicular Technology Conference, 2004, 4 VTC2004-Fall (IEEE), pp. 2611-2615, ISSN: 1090-3038; Kim et al, A new resource allocation scheme based on a PSNR criterion for wireless video transmission to stationary receivers over Gaussian channels, IEEE Transactions on Wireless Communications 1:3, July 2002, pp. 393-401, ISSN: 1536-1276; Raman et al. ITP: an image transport protocol for the Internet, IEEE/ACM Transactions on Networking 10:3, June 2002, pp. 297-307, ISSN 1063-6692; U.S. Pat. Nos. 5,931,904 and 5,276,898.

Generalizing from the above, there remains a need for a system that uses advanced processing to stream medical image data at acceptable quality when available bandwidth is low, and that avoids doing such processing when it is not needed, for example when available bandwidth is high.

SUMMARY OF THE INVENTION

To address the above problems with traditional picture archiving and communications systems, in accordance with the present invention when a user requests an image, a viewer subsystem first determines the available bandwidth or, in some embodiments, other related parameters such as computational resources for pre-/post-processing of images, data type and size, for streaming the image. In the event that high bandwidth is detected relative to the size of the image data, a streaming mode is selected that uses the image in its native (e.g., DICOM) form. In the event that less bandwidth is available, one of several modes is selected for transmission, each requiring less bandwidth but more processing overhead.

In one embodiment, a sequence of lower bandwidth modes includes lossless compression, ROI streaming of pixel data, lossless compression of ROI pixel data, baseline wavelet lossless compression, and progressive wavelet lossless compression.

The features and advantages described in the specification are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The invention has other advantages and features which will be more readily apparent from the following detailed description of certain embodiments of the invention and the appended claims, when taken in conjunction with the accompanying drawings, in which:

DETAILED DESCRIPTION OF THE DRAWINGS

The Figures and the following description relate to embodiments of the present invention by way of illustration only. It should be noted that from the following discussion, alternative embodiments of the structures and methods disclosed herein will be readily recognized as viable alternatives that may be employed without departing from the principles of the claimed invention.

The present invention includes a system and method for transferring medical images in a PACS. In embodiments detailed herein, streaming modes are selected to adapt to given network bandwidth and stability. Where bandwidths are high and stable, simple file transfer of the original image file is used. Where bandwidths are low or the networks unstable, slower and more forgiving modes of transfer are employed.

Figure 1:
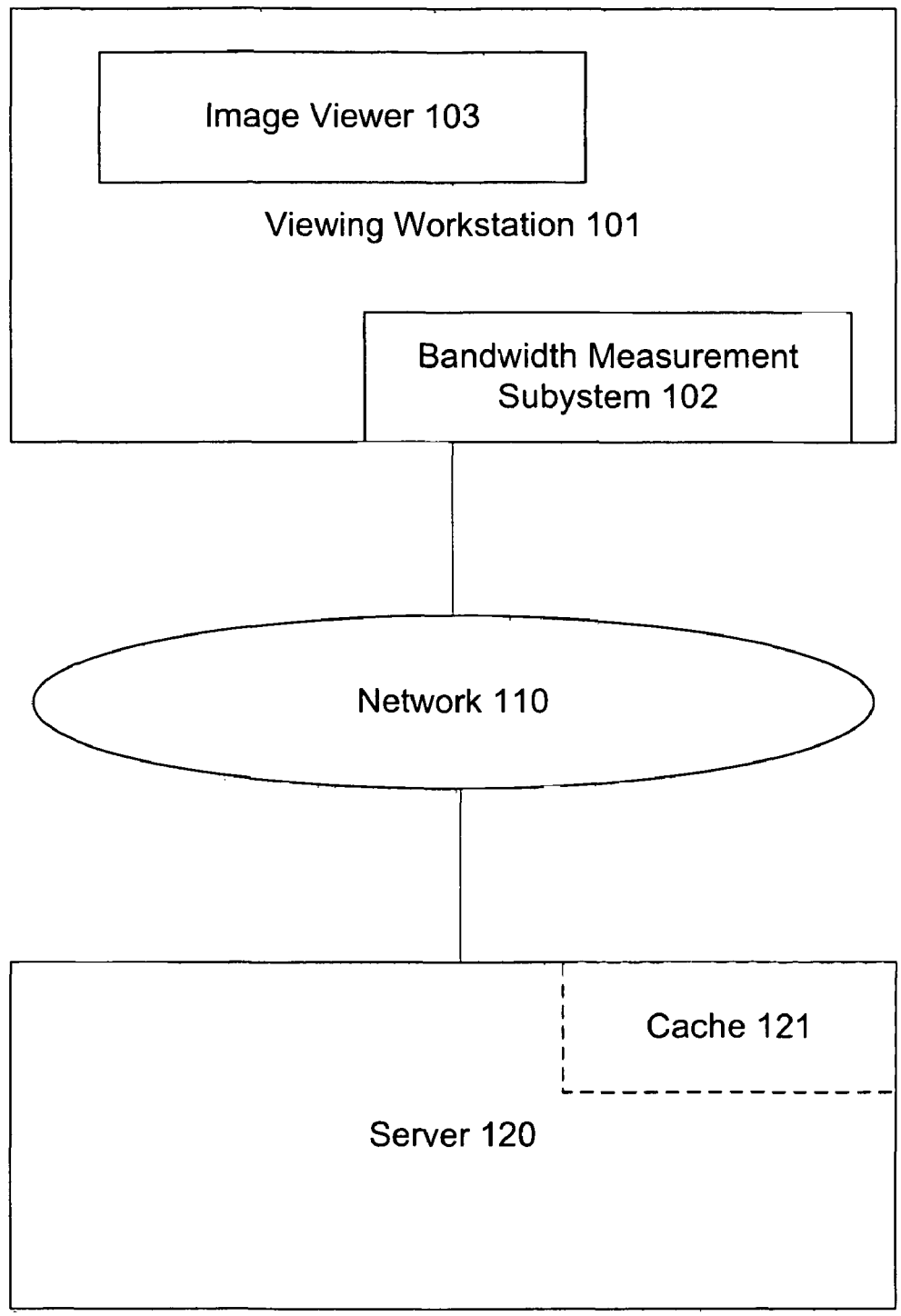
FIG. 1 illustrates in overview fashion interaction among basic components of a system in accordance with the present invention.

Referring now to FIG. 1, a system 100 in accordance with the present invention is shown by way of its basic components: a viewing workstation 101, a network 110 and a server 120. System 100 is configured, as shown, to permit a user at viewing workstation 101 to request a medical image from server 120, the image to be transmitted via network 110. In a typical embodiment, viewing workstation 101 is implemented by a conventional personal computer with appropriate display and network connection, configured as described herein. Likewise, server 120 is implemented by a conventional server computer, such as a Windows operating system personal computer-based server, typically in communication with one or more medical imaging modalities or image storage systems so as to provide a source of medical images. In some embodiments, server 120 includes a cache 121 in which select versions of images are stored. In one embodiment, cache 121 stores images that have not yet been read, with the expectation that a request will be forthcoming for such images. In another embodiment, cache 121 stores compressed versions of images that may have been created by various other processing in the environment in which system 100 operates. Network 110 is, in one embodiment, a conventional data network, for instance an existing local area network or wide area network. In actual installations, it is typical for a health care organization to have a number of viewing workstations 101 and a number of servers 120, interconnected by a variety of networks 110. For example, a radiology clinic may have a viewing workstation connected to an image repository through a dedicated high speed local area network, while a specialty radiologist may from time to time be asked to review images accessible only over a relatively slow and fragile Internet connection from some remote facility.

Furthermore, even a single existing network 110 may have characteristics that change over time. During periods of light usage, the available bandwidth that network 110 provides to a user of viewing workstation 101 may be very large, while at peak times with many users sharing network 110, the available bandwidth may be significantly reduced. In addition to bandwidth, in some embodiments other parameters related to image transfer are evaluated in addition to or instead of bandwidth. In some facilities, different types of images may be stored, each of which has different preferred mechanisms for transfer. If a lossy compressed ultrasound cineloop image is what is stored in server 120, different mechanisms for transfer may be sought than if the image is a high resolution, uncompressed DICOM image. Likewise, it may not be appropriate to use wavelet-based processing as detailed below for images that are stored in JPEG format. For purposes of illustration, the discussion herein will focus on bandwidth as the parameter of interest.

In one embodiment, viewing workstation 101 includes an image viewer subsystem that processes image data received from network 110 and transforms it into a form that can be displayed on viewing workstation 101 for medical diagnosis or any other desired use. Viewing workstation 101 further includes a bandwidth measurement subsystem 102 that determines the expected available bandwidth for image transfer to workstation 101.

Bandwidth measurement subsystem 102 initiates a transfer from server 120 by requesting from the server a small data stream of fixed size. By measuring the amount of time that it takes to transmit the data stream, the bandwidth measurement subsystem 102 estimates the likely bandwidth that will be available for the image transfer. To ensure that the data stream used for measurement is fetched from the server and not some cache of an intermediate proxy server, in one embodiment the subsystem 102 requests slightly different and not readily predictable URLs (web addresses) each time it tests for bandwidth. This is to minimize the likelihood that the information will really be retrieved from server 120, rather than some intermediate cache as may exist somewhere on network 110 between server 120 and viewing workstation 101. In one embodiment, some amount of pseudo-randomness is included in the lowest level of the URL to achieve this result. Furthermore, in one embodiment URLs are selected to minimize the likelihood that the content at that URL will be amenable to significant automatic compression when transmitted from server 120 to network 110. Some networks in which system 100 are used include such automatic compression that, if highly compressible test data were used, would falsely indicate a bandwidth that could not be achieved with real data. In one embodiment, the bandwidth measurement is performed at fixed time intervals, for each server the client is connected to at that given time. In an alternate embodiment, bandwidth measurement subsystem uses historical data for transfers over each of several possible network paths to determine expected bandwidth. In still another embodiment, image transfer is commenced assuming a high, stable bandwidth and actual bandwidth is determined based on image streaming not meeting the expected rate. In still another embodiment, bandwidth measurement is checked occasionally during streaming, so that the streaming mode changes dynamically in response to changes in usable network bandwidth.

As illustrated in FIG. 1, bandwidth measurement subsystem 102 is implemented on viewing workstation 101. In an alternate embodiment, bandwidth measurement subsystem 102 is implemented on server 120 rather than viewing workstation 101. In still a third embodiment, bandwidth measurement subsystem is implemented separately from both viewing workstation 101 and server 120.

Image viewer 103 is configured to process image data in several modes/formats, as further discussed below. Factors influencing the selection of available modes and formats include expected range of network bandwidths and reliability, expected available processing power at both viewing workstation 101 and server 120, and medical practice requirements for the images to be viewed on workstation 101. For example, in some applications, streaming data is computed "on the fly" by server 120, and in those cases processing limitations of server 120 are factors in selection of a particular streaming mode.

Figure 2:
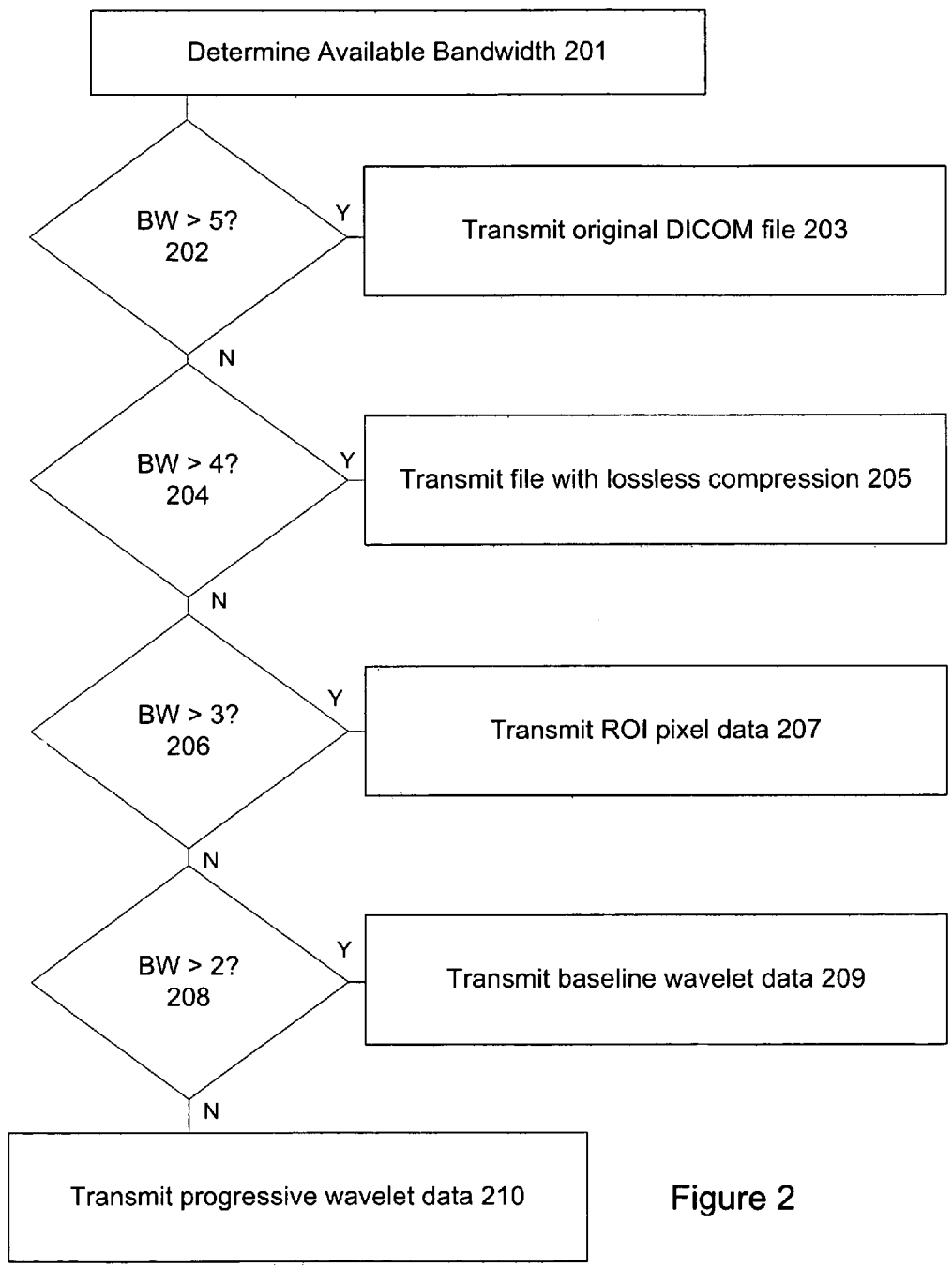
FIG. 2 illustrates a flow diagram for image streaming processing in accordance with the present invention.

Referring now to FIG. 2, a flow diagram of processing in accordance with one embodiment is shown. First, bandwidth measurement subsystem 102 determines the available bandwidth for image transfer, as discussed above. If the bandwidth is above a particular threshold (denoted for convenience as "5" in FIG. 2), viewing workstation 101 requests server 120 to transmit image information in native format, in this instance, the original DICOM file corresponding to the image, and that file is transmitted 203. In this circumstance, transfer of the entire image file is made, regardless of whether the user of workstation 101 has a particular region of interest (ROI) within the image.

If it is determined 205 that the bandwidth is not above the "5" threshold but is above another threshold (denoted as "4" in FIG. 2), workstation 101 requests server 120 to transmit 205 the entire data file in a lossless compression mode. In certain embodiments, compression via conventional efficient, computationally non-intensive methods including lossless JPEG, ZIP and the like are appropriate for this mode of transmission.

Should the bandwidth be determined 206 to be below the "4" threshold but above a "3" threshold, workstation 101 requests server 120 to transmit 207 only the pixels needed for an ROI of the image. In this instance, some additional processing by the server is required, for instance to low-pass filter the image data so as to provide a low-resolution view of the image that will allow selection of the ROI. In one embodiment, the ROI is transmitted with no further processing of the pixels within that ROI; in another embodiment a fast compression scheme is applied to the ROI pixels.

In the event that determination 208 reveals the bandwidth to be below level "3" but above a level "2", then workstation 101 requests server 120 to transmit 209 the image file using baseline wavelet lossless compression. In this mode of transmission, the server codes and streams the image using a moderate computationally demanding wavelet-based algorithm such that visual data can still be streamed in layers of quality or resolution. Examples of such transmission are discussed in U.S. Pat. No. 6,314,452. In this mode, the emphasis is on the ability of the image viewer subsystem 103 to perform fast decoding and rendering of the streamed data. In one embodiment, at this level a wavelet representation of the ROI is encoded using simple variable length coding and transmitted by resolution, and computionally intensive coding components such as arithmetic coding are not used, in order to reduce the overall processing overhead imposed by this transmission. As mentioned above, such management of overhead is needed where server 120 has significant processing limitations.

Should it be determined 208 that the bandwidth is below level 2, the need for processing of the image data increases, and so more processing overhead is accepted. In this instance, workstation 101 requests server 120 to transmit 210 image information using progressive wavelet lossless compression. In this mode the server encodes and streams the ROI in fine layers of visual quality, using computationally intensive methods. This ensures a best possible rate-distortion performance, i.e., that the quality of the image rendered at the client is the best possible for the given amount of data transmitted, at each point in time during the interaction.

In one embodiment, level "5" is a bandwidth of approximately 100 MB/s, level 4 is approximately 50 MB/s, level 3 is approximately 20 MB/s and level 2 is approximately 5 MB/s. In alternate embodiments different numbers of levels, and different thresholds are used. For example, a lower bandwidth denoted as level 1 may be used, in which lossy compression is allowed and the user is warned that the streamed image is lossy. Some medical applications may allow use of such lossy compression, but many will not.

In an alternate embodiment, some image information stored in server 120 may already be in lossy form as well as in lossless form, in which case alternate modes (such as direct transmission of the entire lossy form) may be available for use. In some applications, other processing systems will already have created different versions of image files, for instance lossy compressed versions, for other purposes, and those may be stored in cache 121 for ready access as needed. Should processing overhead on the server side be a concern, such use of cache 121 reduces the need for repeated compression processing by server 120.

The selection of bandwidth thresholds and modes of transmission is not limited to the example discussed above. For example, if workstation 101 has only modest processing capability, modes of transmission that require significant decoding by workstation 101 would be disfavored more than if workstation 101 has robust processing capability.

Similarly, characteristics of the network 120 and of the images themselves will call for particular choices of transmission modes, and thresholds. Should images be very large in comparison with network bandwidth, it may be beneficial to switch to an ROI-based mode more quickly than otherwise.

The selection of mode is not limited to an a priori choice. In one embodiment, a user may adaptively switch among available modes as desired. In another embodiment, mode switching is automatically accomplished when a change in network performance is detected and when actual performance differs from what was originally expected.

The embodiment described above has control implemented on the client side (i.e., at viewing workstation 101). In another embodiment, server 120, or even an external device (not shown) could make bandwidth determinations and mode selections.

In the embodiment described herein, server 120 need only store the original (e.g., DICOM) form of an image, without the need for pre-processing or duplication of data. On the other hand, if such additional versions of the image are already on the server as the result of other processing, those versions are available to be used as well, and may be stored in cache 121.

Upon reading this disclosure, those of skill in the art will appreciate still additional alternative structural and functional designs for a system and process for transactional storage and workflow routing for medical image objects. Thus, while particular embodiments and applications of the present invention have been illustrated and described, it is to be understood that the invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as described in the appended claims.

What is claimed is:

1. An imaging system, comprising:
a server that stores medical image information and transmits the medical image information in a plurality of transmission modes, wherein one transmission mode is a native file format, and each of a remaining transmission modes of the plurality of transmission modes comprise a different compression technique;
a network adapted to transmit the medical image information from the server;
a viewing workstation operatively coupled with the network, the viewing workstation comprising a bandwidth measurement system that initiates a transfer of medical image information from the server to the viewing workstation by estimating an available bandwidth for the transfer of medical image information from the server to the viewing workstation;
wherein the viewing workstation receives the estimate of the available bandwidth from the bandwidth measurement system and selects a transmission mode from the plurality of transmission modes, the plurality of transmission modes organized in a hierarchy of transmission modes, each of the transmission modes of the plurality being associated with a threshold bandwidth value, and the viewing workstation selects the transmission mode from the plurality of transmission modes by comparing the estimate of the available bandwidth to a plurality of threshold bandwidth values;

wherein the viewing workstation requests transmission of the medical image information from the server and the viewing workstation requests the selected transmission mode for a transmission of the medical image information from the server;

wherein if the selected transmission mode is one of the remaining transmission modes, the server compresses the medical image information in accordance with the compression technique of the requested transmission mode, and transmits the medical image information to the viewing workstation.

2. An imaging system as in claim 1, wherein the plurality of transmission modes includes transmission of original image files, transmission of losslessly compressed image file data, transmission of region of interest pixel data, transmission of wavelet lossless compression image file data, and transmission of region of interest wavelet lossless compression data.

3. An imaging system as in claim 1, wherein the plurality of modes includes transmission of a lossy compressed version of image data in response to the server having pre-existing access to the lossy compressed version.

4. An imaging system as in claim 1, wherein the viewing workstation is configured to request transmission in said one of the plurality of modes responsive to performance characteristics of the viewing workstation relative to characteristics of the medical image information.

5. A method of transmitting medical image information within a picture archiving and communications system (PACS) including a server communicatively coupled to a viewing workstation via a communications network, the method comprising:

storing medical image information at the server;

initiating a transfer of medical image information from the server to the viewing workstation with the viewing workstation;

determining, an available bandwidth of the communications network, with a bandwidth measurement system, between the server and the viewing workstation;

establishing, with the viewing workstation, a hierarchy of transmission modes wherein each of the transmission modes in the hierarchy is associated with a threshold bandwidth value;

selecting, with the viewing workstation, a transmission mode from a plurality of transmission modes wherein one transmission mode of the plurality is a native file format and each of a remaining transmission modes of the plurality comprise a different compression technique, the selection of the transmission mode includes comparing the determined bandwidth of the communications network to a plurality of threshold bandwidth values;

requesting, from the viewing workstation to the server, the transfer of specified medical image information from the server to the viewing workstation;

requesting, from the viewing workstation to the server, the selected transmission mode for the transfer of the specified medical image information from the server to the viewing workstation; and processing the medical image information with the server into the selected transmission mode;

transmitting the medical image information in the selected transmission mode from the server to the viewing workstation via the communications network.

6. A method as in claim 5, further comprising:

determining, with the server, a pre-processing capability of the server;

determining, with the viewing workstation, a post-processing capability of the viewing workstation;

providing the pre-processing capability of the server to the viewing workstation and wherein the viewing workstation determines the plurality of threshold bandwidth values based upon the pre-processing and post-processing capabilities each threshold bandwidth value of the plurality is associated with one of the plurality of transmission modes.

7. A method as in claim 6, wherein selecting includes the viewing workstation selecting a transmission mode associated with a highest threshold value met by the bandwidth.

8. The method of claim 5, wherein each of the transmission modes in the hierarchy is associated with a threshold bandwidth value, and the viewing workstation selects a transmission mode from the hierarchy that is associated with the highest threshold bandwidth value achieved by the determined bandwidth of the communications network.

9. The method of claim 7, further comprising continuously determining the bandwidth of the network wherein a change in the determined bandwidth of the network results in the viewing workstation selecting a different transmission mode of the plurality of transmission modes.

10. The method of claim 8, wherein the hierarchy of transmission modes comprises, in descending order, based upon the threshold bandwidth value: transmission of original image files, transmission of losslessly compressed image file data, transmission of region of interest pixel data, transmission of wavelet lossless compression image data, transmission of region of interest wavelet lossless compression image data, transmission of lossy compression image data, and transmission of compressed region of interest image data.

11. The method of claim 5, further comprising:

requesting with the bandwidth measurement system a data stream of a fixed size from the server;

transmitting the data stream from the server to the bandwidth measurement system;

measuring a time with the bandwidth measurement system for the transmission of the data stream to the bandwidth measurement system;

wherein the bandwidth of the network is estimated based upon the measured time.

12. The method of claim 11, wherein the bandwidth measurement system requests the data stream of a fixed size from a different URL each time the bandwidth of the network is estimated further comprising a test URL with the bandwidth measurement system for the data stream, wherein the test URL is fetched to minimize the transmission of cached data.

13. The method of claim 12, wherein each possible URL for the data stream request contains pseudo-randomness.

14. The method of claim 5, further comprising:

determining with the viewing workstation, an identification of an image type of the medical image information; and wherein the selection of the transmission mode is further based upon the identification of the image type.

15. The system of claim 1, further comprising a plurality of servers that each store medical image information, each of the plurality of servers are communicatively connected to the viewing workstation by the network wherein the viewing workstation initiates a transfer of medical image information from a one server of the plurality of servers to the viewing workstation and the bandwidth measurement subsystem estimates an available bandwidth across the network between the one server and the viewing workstation, the viewing workstation requests the medical image information and the selected transmission mode for the transmission of medical image information from the one server to the viewing workstation.

16. The system of claim 15, wherein the estimated available bandwidth is between the viewing workstation and the one server independent from to an estimated bandwidth between the viewing workstation and each of the other servers of the plurality.

17. The method of claim 5, wherein the PACS includes a plurality of servers communicatively coupled to the viewing workstation via the communications network, and wherein determining the bandwidth of the communications network comprises determining the bandwidth of the communications network between the viewing workstation and a server of the plurality of servers and the viewing workstation requests the transfer of specified medical image information and the selected transmission mode to the server of the plurality of servers for the transmission of the specified medical image information from the server of the plurality of servers to the viewing workstation.

* * * * *